(12) United States Patent
Lee et al.

(10) Patent No.: US 8,029,531 B2
(45) Date of Patent: Oct. 4, 2011

(54) SURGICAL INSTRUMENT

(75) Inventors: Woojin Lee, Hopkinton, MA (US);
Andres Chamorro, Natick, MA (US);
Woojoong Lee, The Bottom (AN)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 1239 days.

(21) Appl. No.: 11/528,134

(22) Filed: Sep. 27, 2006

(65) Prior Publication Data
US 2008/0015631 A1 Jan. 17, 2008

Related U.S. Application Data

(60) Provisional application No. 60/830,035, filed on Jul. 11, 2006.

(51) Int. Cl.
*A61B 17/00* (2006.01)
(52) U.S. Cl. ...................................... 606/205
(58) Field of Classification Search .......... 606/139–146, 606/205–206; 446/378; 600/141, 142, 148; 604/528
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |
| 2,790,437 A | 4/1957 | Moore | |
| 3,107,954 A | 10/1963 | Rudy | |
| 3,557,780 A | 1/1971 | Sato | |
| 3,858,577 A | 1/1975 | Bass et al. | |
| 3,895,636 A | 7/1975 | Schmidt | |
| 4,483,562 A | 11/1984 | Schoolman | |
| 4,483,579 A | 11/1984 | Derr et al. | |

(Continued)

FOREIGN PATENT DOCUMENTS

EP 0 095 970 A2 12/1983

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Gary Jackson
*Assistant Examiner* — Eric Blatt
(74) *Attorney, Agent, or Firm* — David M. Driscoll, Esq.

(57) ABSTRACT

A surgical instrument that includes an instrument shaft having proximal and distal ends, a tool disposed from the distal end of the instrument shaft, a control handle disposed from the proximal end of the instrument shaft, a distal motion member for coupling the distal end of the instrument shaft to the tool, a proximal motion member for coupling the proximal end of the instrument shaft to the handle, actuation means extending between the distal and proximal motion members for coupling motion of the proximal motion member to the distal motion member for controlling the positioning of the tool, a rotation knob disposed adjacent the control handle and rotatable relative to the control handle for causing a corresponding rotation of the instrument shaft and tool and a locking mechanism for fixing the position of the tool at a selected position and having locked and unlocked states. The rotation knob has a first position in which the locking mechanism is controlled to be in its locked state and a second position in which the locking mechanism is released to its unlocked state so as to allow tool positioning.

40 Claims, 6 Drawing Sheets

U.S. PATENT DOCUMENTS

| | | | |
|---|---|---|---|
| 4,531,855 A | 7/1985 | Wallis | |
| 4,554,798 A * | 11/1985 | D'Amour et al. | 62/457.5 |
| 4,688,554 A | 8/1987 | Habib | |
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nierman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshaw et al. | |
| 5,042,707 A | 8/1991 | Taheri | |
| 5,209,747 A | 5/1993 | Knoepfler | |
| 5,251,611 A | 10/1993 | Zehel et al. | |
| 5,254,130 A | 10/1993 | Poncet et al. | |
| 5,271,381 A | 12/1993 | Ailinger et al. | |
| 5,273,026 A | 12/1993 | Wilk | |
| 5,275,608 A | 1/1994 | Forman et al. | |
| 5,314,424 A | 5/1994 | Nicholas | |
| 5,330,502 A | 7/1994 | Hassler et al. | |
| 5,344,428 A | 9/1994 | Griffiths | |
| 5,383,880 A | 1/1995 | Hooven | |
| 5,386,818 A | 2/1995 | Schneebaum et al. | |
| 5,391,180 A | 2/1995 | Tovey et al. | |
| 5,395,367 A | 3/1995 | Wilk | |
| 5,405,344 A | 4/1995 | Williamson et al. | |
| 5,417,203 A | 5/1995 | Tovey et al. | |
| 5,433,721 A | 7/1995 | Hooven et al. | |
| 5,441,494 A | 8/1995 | Ortiz | |
| 5,454,827 A | 10/1995 | Aust et al. | |
| 5,501,654 A | 3/1996 | Failla et al. | |
| 5,508,712 A | 4/1996 | Tom et al. | |
| 5,520,678 A | 5/1996 | Heckele et al. | |
| 5,556,416 A | 9/1996 | Clark et al. | |
| 5,599,151 A | 2/1997 | Daum et al. | |
| 5,618,294 A | 4/1997 | Aust et al. | |
| 5,624,381 A | 4/1997 | Kieturakis | |
| 5,643,294 A | 7/1997 | Tovey et al. | |
| 5,665,105 A * | 9/1997 | Furnish et al. | 606/205 |
| 5,702,408 A | 12/1997 | Wales et al. | |
| 5,743,496 A | 4/1998 | Atkinson, Jr. | |
| 5,759,151 A | 6/1998 | Sturges | |
| 5,766,196 A | 6/1998 | Griffiths | |
| 5,772,578 A | 6/1998 | Heimberger et al. | |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,899,425 A | 5/1999 | Corey, Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,928,263 A | 7/1999 | Hoogeboom | |
| 5,938,678 A | 8/1999 | Zirps et al. | |
| 5,944,713 A | 8/1999 | Schuman | |
| 5,987,757 A * | 11/1999 | Schmidt et al. | 30/341 |
| 6,126,633 A | 10/2000 | Kaji et al. | |
| 6,147,650 A | 11/2000 | Kawahata et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,210,416 B1 | 4/2001 | Chu et al. | |
| 6,270,453 B1 | 8/2001 | Sakai | |
| 6,352,227 B1 | 3/2002 | Hathaway | |
| 6,551,238 B2 | 4/2003 | Staud | |
| 6,623,424 B2 | 9/2003 | Hayakawa et al. | |
| 6,638,214 B2 | 10/2003 | Akiba | |
| 6,641,316 B1 | 11/2003 | Goldstein et al. | |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 6,889,116 B2 | 5/2005 | Jinno | |
| 7,073,822 B1 | 7/2006 | Renfroe et al. | |
| 7,090,637 B2 | 8/2006 | Danitz | |
| 7,147,650 B2 | 12/2006 | Lee | |
| 7,320,700 B2 | 1/2008 | Cooper et al. | |
| 7,338,513 B2 | 3/2008 | Lee et al. | |
| 7,364,582 B2 | 4/2008 | Lee | |
| 7,615,067 B2 | 11/2009 | Lee et al. | |
| 7,648,519 B2 | 1/2010 | Lee et al. | |
| 7,678,117 B2 | 3/2010 | Hinman et al. | |
| 7,682,307 B2 | 3/2010 | Danitz et al. | |
| 7,686,826 B2 | 3/2010 | Lee et al. | |
| 7,708,758 B2 | 5/2010 | Lee et al. | |
| 7,785,252 B2 | 8/2010 | Danitz et al. | |
| 7,842,028 B2 | 11/2010 | Lee | |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0171650 A1 | 9/2003 | Tartaglia et al. | |
| 2003/0216618 A1 | 11/2003 | Arai | |
| 2003/0216619 A1 | 11/2003 | Scirica et al. | |
| 2003/0225364 A1 | 12/2003 | Kraft et al. | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0096694 A1 | 5/2005 | Lee | |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman et al. | |
| 2005/0273085 A1 | 12/2005 | Hinman et al. | |
| 2006/0095074 A1 | 5/2006 | Lee et al. | |
| 2006/0195097 A1 | 8/2006 | Evans et al. | |
| 2006/0206101 A1 | 9/2006 | Lee | |
| 2006/0270909 A1 | 11/2006 | Davis et al. | |
| 2007/0021737 A1 | 1/2007 | Lee | |
| 2007/0250110 A1 | 10/2007 | Lu et al. | |
| 2007/0276430 A1 | 11/2007 | Lee et al. | |
| 2008/0255420 A1 | 10/2008 | Lee et al. | |
| 2008/0294191 A1 | 11/2008 | Lee | |
| 2009/0069842 A1 | 3/2009 | Lee et al. | |
| 2009/0171147 A1 | 7/2009 | Lee et al. | |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| JP | 2002 102248 | 4/2002 |
| JP | 2003 135473 | 5/2003 |
| WO | WO 90/05491 | 5/1990 |
| WO | WO 92/01414 | 2/1992 |
| WO | WO 94/17965 | 8/1994 |
| WO | 97 23158 | 7/1997 |
| WO | 02 13682 | 2/2002 |
| WO | 2004 105578 | 12/2004 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

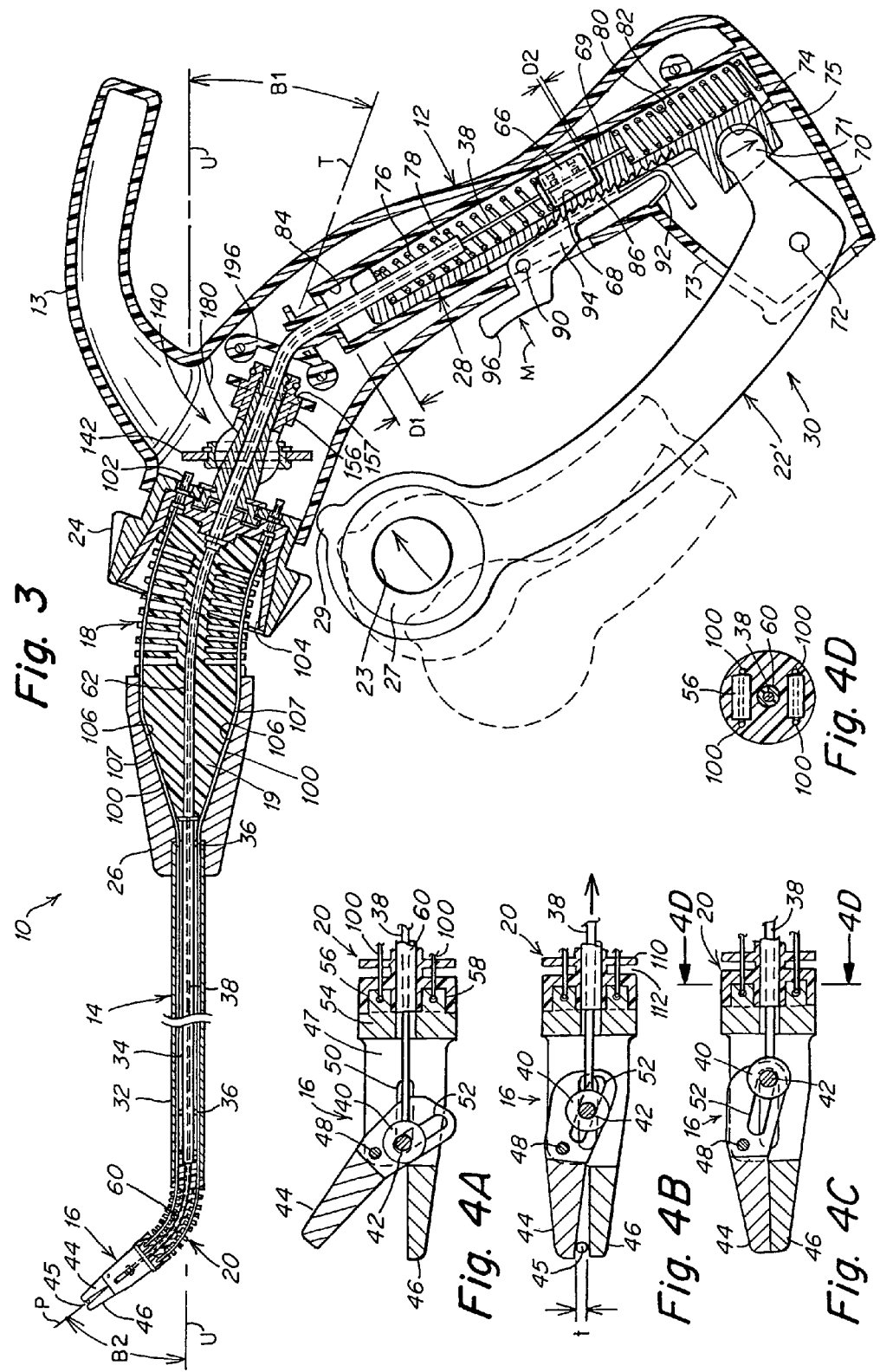

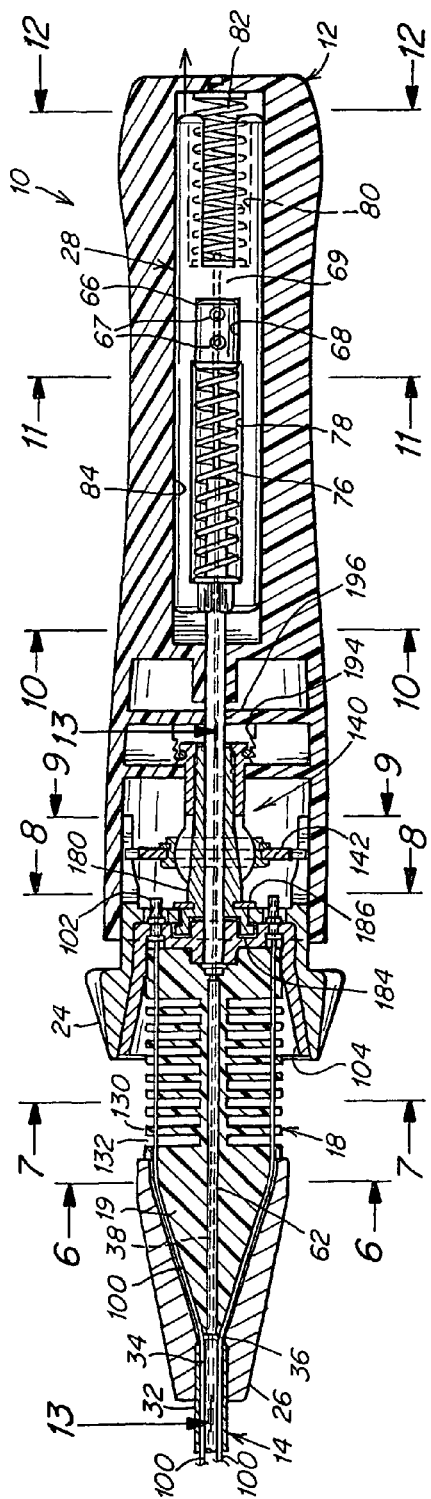
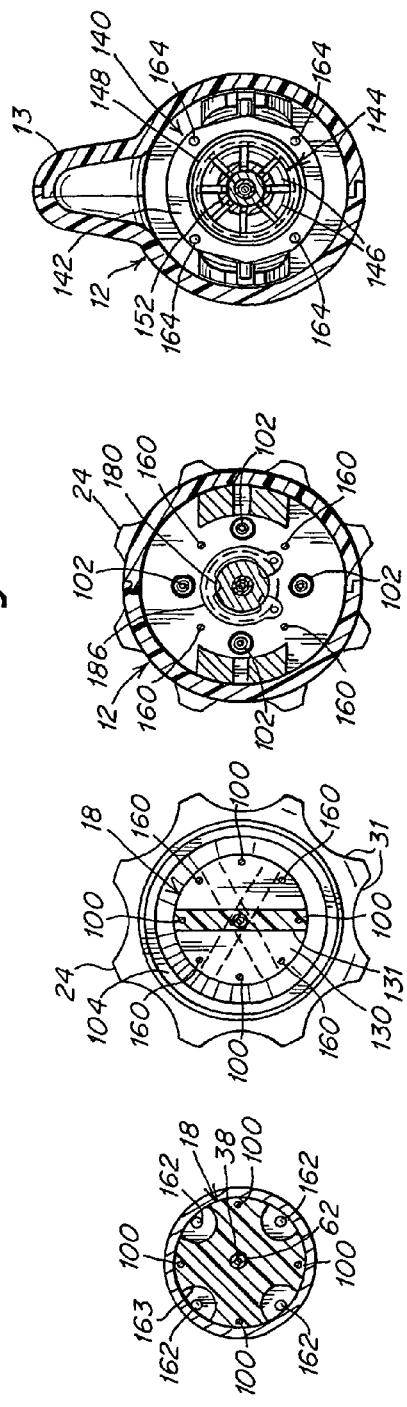
Fig. 5
Fig. 9
Fig. 8
Fig. 7
Fig. 6

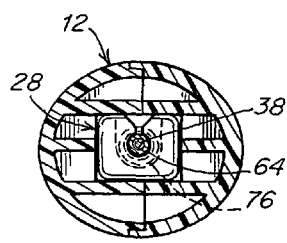
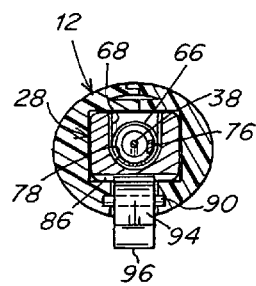
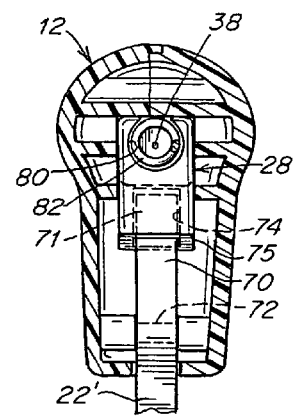
Fig. 10   Fig. 11   Fig. 12
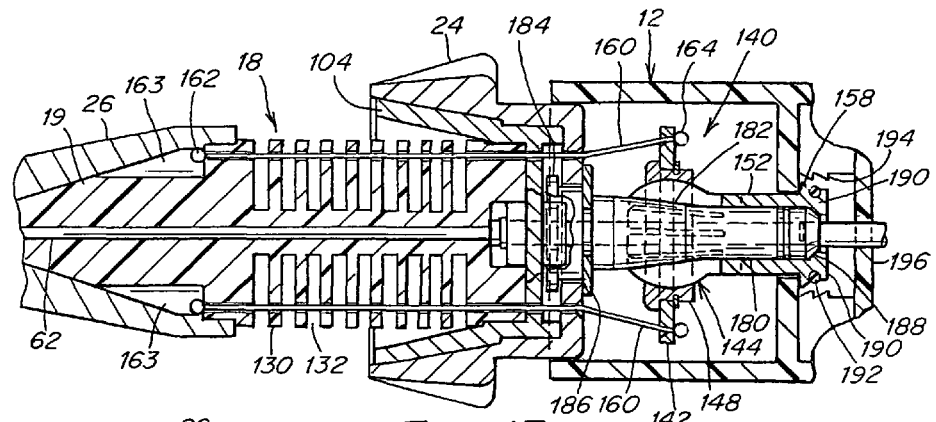
Fig. 13
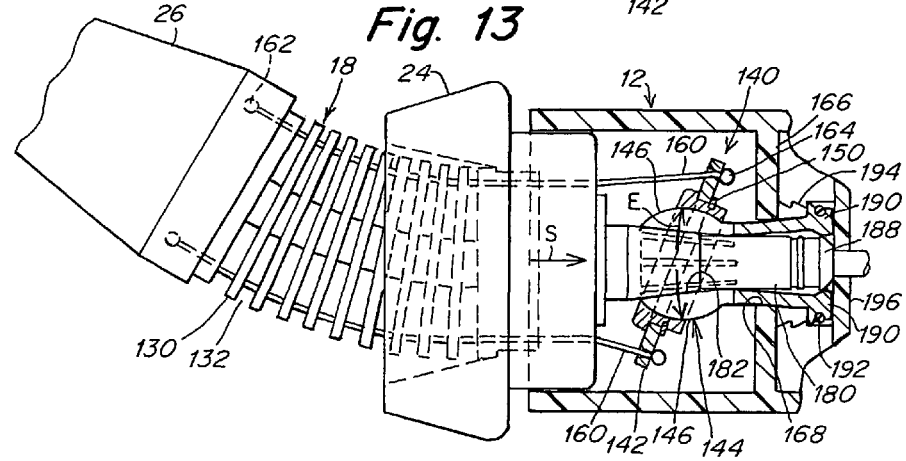
Fig. 14

SURGICAL INSTRUMENT

RELATED APPLICATION

Priority for this application is hereby claimed under 35 U.S.C. §119(e) to commonly owned and co-pending U.S. Provisional Patent Application No. 60/830,035 which was filed on Jul. 11, 2006. The content of all of the aforementioned application is hereby incorporated by reference herein in its entirety.

TECHNICAL FIELD

The present invention relates in general to surgical instruments, and more particularly to manually-operated surgical instruments that are intended for use in minimally invasive surgery or other forms of surgical or medical procedures or techniques. The instrument described herein is primarily for a laparoscopic procedure, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position. Moreover, existing instruments require the use of both hands in order to effectively control the instrument.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical or medical instrument that has a wide variety of applications, through incisions, through natural body orifices or intraluminally.

A further object of the present invention is to provide an improved medical instrument that is characterized by the ability to lock the instrument in a pre-selected particular position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved medical instrument that can be effectively controlled with a single hand of the user.

Still a further object of the present invention is to provide an improved medical instrument in which both locking and rotation features of the instrument are controlled from a single control element.

SUMMARY OF THE INVENTION

To accomplish the foregoing and other objects, features and advantages of the present invention there is provided a surgical instrument that includes an instrument shaft having proximal and distal ends; a tool disposed from the distal end of the instrument shaft; a control handle disposed from the proximal end of the instrument shaft; a distal motion member for coupling the distal end of said instrument shaft to said tool; a proximal motion member for coupling the proximal end of said instrument shaft to said handle; actuation means extending between said distal and proximal motion members for coupling motion of said proximal motion member to said distal motion member for controlling the positioning of said tool; a rotation knob disposed adjacent the control handle and rotatable relative to the control handle for causing a corresponding rotation of the instrument shaft and tool; and a locking mechanism for fixing the position of the tool at a selected position and having locked and unlocked states. The rotation knob has a first position in which the locking mechanism is controlled to be in its locked state and a second position in which the locking mechanism is released to its unlocked state so as to allow tool positioning.

In accordance with other aspects of the present invention at least the proximal motion member comprises a proximal bendable member and the rotation knob is adapted to rotate the tool about a distal tool roll axis; the control handle comprises a pistol grip handle having an engagement horn to assist in holding the handle; the rotation knob is disposed at the distal end of the handle and the horn is disposed proximally of the rotation knob and on the top of the pistol grip handle; including an actuation lever supported from the pistol grip handle at a pivot point at the proximal end of the handle; the actuation lever has a free end with a finger loop for receiving a users finger to control the lever; further including a release button on the handle in juxtaposition to the lever and for releasing the lever from an actuated to released position; the rotation knob is supported relative to the handle so as to rotate about a rotation knob axis, and wherein the rotation knob is moved axially from the first to second positions; the rotation knob is moved toward the handle to activate the locking mechanism and is moved away from the handle to release the locking mechanism; including a tool actuation cable that extends from the tool to the handle, a slider for capturing the proximal end of said tool actuation cable and an actuation lever supported at the handle for controlling the translation of the slider; including a slideway for receiving the slider, a pair of springs disposed in the slider and a rotational barrel disposed between the springs and for holding the proximal end of the tool actuation cable; the locking mechanism comprises a follower mechanism disposed proximally of the rotation knob, the proximal motion member comprising a proximal bendable member and a plurality of locking cables that intercouple between the follower mechanism and the proximal bendable member; the locking mechanism further comprises an expandable sphere for supporting the locking cables and a plunger engaging with a center passage of the expandable sphere, the plunger supported from the rotation knob.

In accordance with another embodiment of the present invention there is provided a surgical instrument comprising: an instrument shaft having proximal and distal ends; a tool disposed from the distal end of the instrument shaft; a control handle disposed from the proximal end of the instrument shaft; a distal motion member for coupling the distal end of the instrument shaft to the tool; a proximal motion member for coupling the proximal end of the instrument shaft to the handle; actuation means extending between the distal and proximal motion members for coupling motion of the proximal motion member to the distal motion member for controlling the positioning of the tool; said control handle including a pistol grip handle; and an actuation lever for controlling the tool and pivotally supported from the handle; said actuation lever having a free end with a recess for receiving a finger of the user to control the actuation lever.

In accordance with other aspects of the present invention the surgical instrument includes a ball supported in a socket at the free end of the actuation lever, said ball having a hole therein that defines the finger recess; the ball is freely rotatable in the socket and the hole is a through hole; the ball is freely rotatable in the socket and the hole is a blind hole; a release button on the handle is in juxtaposition to the lever and for releasing the lever from an actuated to released position; a rotation knob is disposed adjacent the control handle and rotatable relative to the control handle for causing a corresponding rotation of the instrument shaft and tool, and a locking mechanism for fixing the position of the tool at a selected position and having locked and unlocked states, said rotation knob having a first position in which the locking mechanism is controlled to be in its locked state and a second position in which the locking mechanism is released to its unlocked state so as to allow tool positioning; the rotation knob is supported relative to the handle so as to rotate about a rotation knob axis, and wherein the rotation knob is moved axially from the first to second positions; an engagement horn to assist in holding the handle and wherein the rotation knob is disposed at the distal end of the handle and the horn is disposed proximally of the rotation knob and on the top of the pistol grip handle.

In accordance with still another embodiment there is provided a medical instrument having a proximal control handle and a distal tool that are intercoupled by an elongated instrument shaft that is meant to pass internally of an anatomic body, proximal and distal movable members that respectively intercouple the proximal control handle and the distal tool with the instrument shaft, cable actuation means disposed between the movable members, said control handle having proximal and distal ends, an actuation lever for controlling the distal tool, means for pivotally supporting the actuation lever from the proximal end of the handle at one side thereof, a horn and means for fixedly supporting the horn from the distal end of the handle at an opposite side thereof.

In accordance with still other aspects of the present invention the medical instrument includes a locking means that is manually operable by a user and that includes a follower the position of which is responsive to the position of the movable members; a rotation knob is disposed adjacent the control handle and rotatable relative to the control handle for causing a corresponding rotation of the instrument shaft and tool, and a locking mechanism for fixing the position of the tool at a selected position and having locked and unlocked states, said rotation knob having a first position in which the locking mechanism is controlled to be in its locked state and a second position in which the locking mechanism is released to its unlocked state so as to allow tool positioning; the rotation knob is supported relative to the handle so as to rotate about a rotation knob axis, and wherein the rotation knob is moved axially from the first to second positions; the control handle includes a pistol grip handle and the actuation lever has a free end with a recess for receiving a finger of the user to control the actuation lever; a ball is supported in a socket at the free end of the actuation lever, said ball having a hole therein that defines the finger recess; including a rotation control member at the distal end of the handle, said horn disposed adjacent to the rotation control member, said actuation lever supported for movement toward and away from the handle; including a release button on the handle in juxtaposition to the lever and for releasing the lever from an actuated to released position; including a slider in the handle for controlling a tool actuation cable, said lever including a pivot point attached to the handle and disposed between one end that defines a socket for a rotation gimbal for accommodating the user's finger and another end that engages the slider.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIG. 3 is an enlarged cross-sectional side view of the instrument shown in FIG. 2 showing the end effector bent at an angle B2 in response to the handle being bent at an angle B1, and with the end effector in a closed position grasping an item;

FIGS. 4A-4C are illustrative cross-sectional side views at the distal end of the medical instrument, and with the movable jaw in different respective positions;

FIG. 4D is a cross-sectional view taken along line 4D-4D of FIG. 4C;

FIG. 5 is a cross-sectional plan view of the handle portion of the instrument of the second embodiment as taken along line 5-5 of FIG. 2;

FIG. 6 is a cross-sectional end view taken along line 6-6 of FIG. 5;

FIG. 7 is a cross-sectional end view taken along line 7-7 of FIG. 5;

FIG. 8 is a cross-sectional end view taken along line 8-8 of FIG. 5;

FIG. 9 is a cross-sectional end view taken along line 9-9 of FIG. 5;

FIG. 10 is a cross-sectional end view taken along line 10-10 of FIG. 5;

FIG. 11 is a cross-sectional end view taken along line 11-11 of FIG. 5;

FIG. 12 is a cross-sectional end view taken along line 12-12 of FIG. 5;

FIG. 13 is a fragmentary enlarged cross-sectional plan view taken along line 13-13 of FIG. 5 showing the proximal bendable member and angled locking mechanism at rest;

FIG. 14 is a cross-sectional view similar to that shown in FIG. 13, but with the proximal bendable member locked in an angled relationship to the handle;

DETAILED DESCRIPTION OF THE PREFERRED EMBODIMENT

The instrument of the present invention may be used to perform minimally invasive procedures. "Minimally invasive procedure," refers herein to a surgical procedure in which a surgeon operates through small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen or vessel, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thorasic, prostate, transvaginal and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

Figure 1:
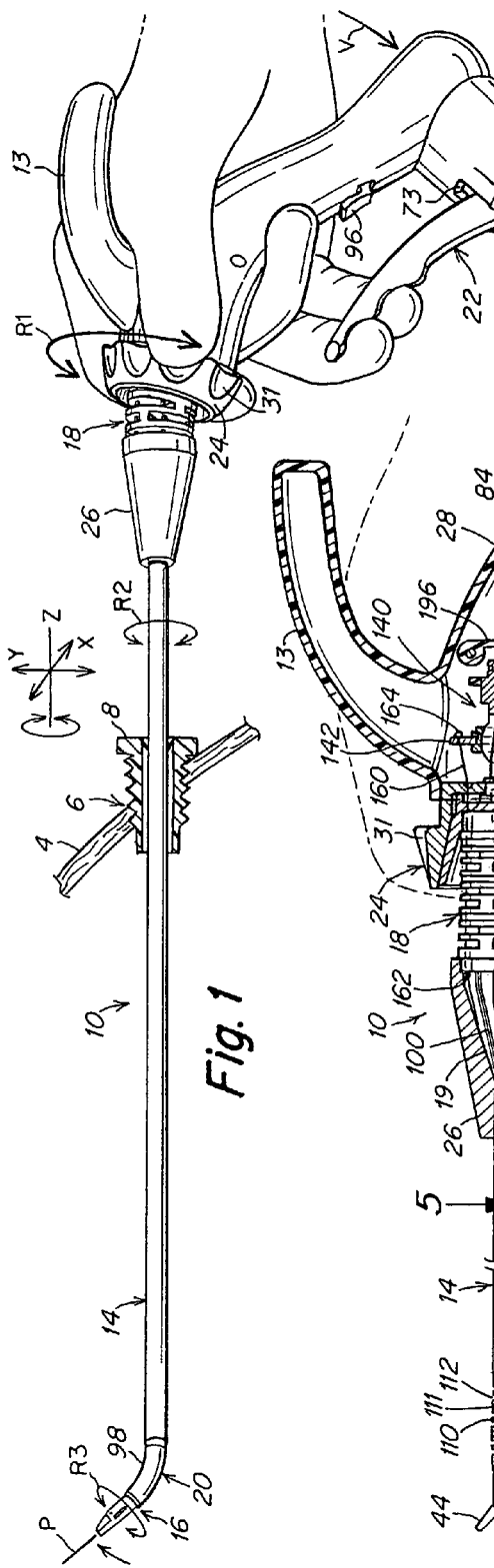
FIG. 1 is a perspective view of a first embodiment of the surgical instrument of the present invention illustrating it being grasped by a surgeon.

FIG. 1 is a perspective view of one embodiment of the surgical instrument 10 of the present invention. In this surgical instrument both the tool and handle motion members or bendable members are capable of bending in any direction. They are interconnected via cables in such a way that a bending action at the proximal member provides a related bending at the distal member. The proximal bending is controlled by a motion or deflection of the control handle by a user of the instrument. In other words the surgeon grasps the handle and once the instrument is in position any motion at the handle (deflection) immediately controls the proximal bendable member which, in turn, via cabling controls a corresponding bending or deflection at the distal bendable member. This action, in turn, controls the positioning of the distal tool.

The proximal member is preferably generally larger than the distal member so as to provide enhanced ergonomic control. In one version in accordance with the invention there may be provided a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

It should be noted that the amount of bending motion produced at the distal bending member is determined by the dimension of the proximal bendable member in comparison to that of the distal bendable member. In the embodiment described the proximal bendable member is generally larger than the distal bendable member, and as a result, the magnitude of the motion produced at the distal bendable member is greater than the magnitude of the motion at the proximal bendable member. The proximal bendable member can be bent in any direction (about 360 degrees) controlling the distal bendable member to bend in either the same or an opposite direction, but in the same plane at the same time. Also, as depicted in FIG. 1, the surgeon is able to bend and roll the instrument's tool about its longitudinal axis at any orientation simply by rolling the axial rotation knob.

In this description reference is made to bendable members. These members may also be referred to as turnable members, bendable members or flexible members. In the descriptions set out herein, terms such as "bendable section," "bendable segment," "bendable motion member," or "tunable member" refer to an element of the instrument that is controllably bendable in comparison to an element that is pivoted at a joint. The term "movable member" is considered as generic to bendable sections and joints. The bendable elements of the present invention enable the fabrication of an instrument that can bend in any direction without any singularity and that is further characterized by a ready capability to bend in any direction, all preferably with a single unitary or uni-body structure. A definition of a "unitary" or "uni-body" structure is—a structure that is constructed only of a single integral member and not one that is formed of multiple assembled or mated components—.

A definition of these bendable motion members is—an instrument element, formed either as a controlling means or a controlled means, and that is capable of being constrained by tension or compression forces to deviate from a straight line to a curved configuration without any sharp breaks or angularity—. Bendable members may be in the form of unitary structures, such as shown herein in FIG. 2, may be constructed of engageable discs, or the like, may include bellows arrangements or may comprise a movable ring assembly. For other forms of bendable members refer to co-pending provisional applications Ser. No. 60/802,885 filed on May 23, 2006 and 60/811,046 filed on Jun. 5, 2006, both of which are hereby incorporated by reference herein in their entirety.

FIG. 1 shows a first embodiment of the instrument of the present invention. A second preferred embodiment is illustrated in FIGS. 2-16. FIG. 1 depicts the surgical instrument 10 in position, as may occur during a surgical procedure. For example, the instrument may be used for laparoscopic surgery through the abdominal wall 4. For this purpose there is provided an insertion site 6 at which there is disposed a cannula or trocar 8. The shaft 14 of the instrument 10 is adapted to pass through the cannula 8 so as to dispose the distal end of the instrument at an operative site. The end effector 16 is depicted in FIG. 1 at such an operative site. FIG. 1 also depicts the rolling motion that can be carried out with the instrument of the present invention. This can occur by virtue of the rotation of the rotation knob 24 relative to the handle 12 about axis T (refer to FIG. 3). This is illustrated in FIG. 1 by the circular arrow R1. Also see in FIG. 1 the coordinate X-Y-Z system. The Z axis corresponds to the longitudinal axis of the instrument shaft 14. When the rotation knob 24 is rotated, in either direction, this causes a corresponding rotation of the instrument shaft 14. This is depicted in FIG. 1 by the rotational arrow R2. This same motion also causes a rotation of the end effector 16 about axis P as illustrated by the rotational arrow R3.

Any rotation of the rotation knob 24 while the instrument is locked (or unlocked) maintains the instrument tip at the same angular position, but rotates the orientation of the tip (tool). For a further explanation of the rotational feature refer to co-pending application Ser. No. 11/302,654, filed on Dec. 14, 2005, particularly FIGS. 25-28, which is hereby incorporated by reference in its entirety.

In FIG. 3 the handle 12, via proximal bendable member 18, is shown tilted along axis T at an angle B1 to the instrument shaft longitudinal center axis U. This tilting, deflecting or bending may be considered as in the plane of the paper. By means of the cabling this action causes a corresponding bend at the distal bendable member 20 to a position wherein the tip is directed along axis P and at an angle B2 to the instrument shaft longitudinal center axis U. The bending at the proximal bendable member 18 is controlled by the surgeon from the handle 12 by manipulating the handle in essentially any direction including in and out of the plane of the paper in FIG. 3. This manipulation directly controls the bending at the proximal bendable member.

Thus, the control at the handle is used to bend the instrument at the proximal motion member to, in turn, control the positioning of the distal motion member and tool. The "position" of the tool is determined primarily by this bending or motion action and may be considered as the coordinate location at the distal end of the distal motion member. Actually, one may consider a coordinate axis at both the proximal and distal motion members as well as at the instrument tip. This positioning is in three dimensions. The "orientation" of the tool, on the other hand, relates to the rotational positioning of the tool about the illustrated distal tip axis (see axis P in FIG. 3).

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

The surgical instrument of FIG. 1 shows a first embodiment of a surgical instrument 10 according to the invention in use and inserted through a cannula 8 at an insertion site 6 through a patient's skin. Many of the components shown in both embodiments described herein, such as the instrument shaft 14, end effector 16, distal bending member 20, and proximal bending member 18 may be similar to and interact in the same manner as the instrument components described in the co-pending U.S. application Ser. No. 11/185,911 filed on Jul. 20, 2005 and hereby incorporated by reference herein in its entirety. Also incorporated by reference in their entirety are U.S. application Ser. No. 10/822,081 filed on Apr. 12, 2004; U.S. application Ser. No. 11/242,642 filed on Oct. 3, 2005 and U.S. application Ser. No. 11/302,654 filed on Dec. 14, 2005, all commonly owned by the present assignee.

Figure 2:
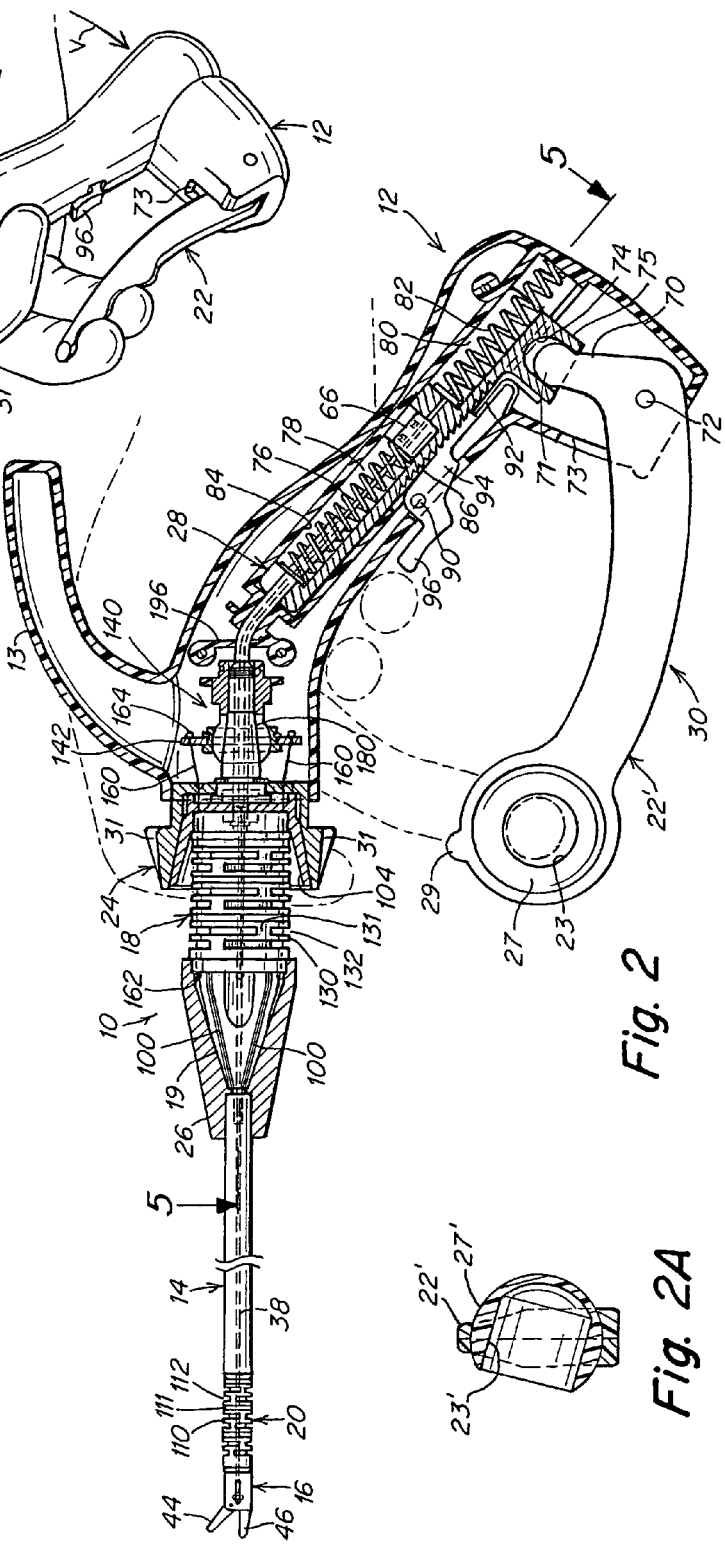
FIG. 2 is a cross-sectional side view of a second embodiment of the instrument of the present invention with the instrument in its rest position and illustrating in phantom the surgeon's fingers.

The first embodiment of the instrument shown in FIG. 1 is typically used with a sheath 98 to keep bodily fluids from entering the distal bending member 20. The rotation knob 24, proximal bending member 18 and adapter 26 accommodate preferably four bend control cables, as well as four lock control cables which are connected to a novel angle locking means or follower 140 which is supported adjacent the proximal end of the rotation knob 24, as depicted in FIG. 2. The locking means interacts with a portion of the proximal bendable member 18 to lock and unlock the positioning of the bend control cables which in turn control the angle of the proximal bending member and thus the angle of the distal bendable member and end effector. This lock control allows the surgeon one less degree of control to concentrate on when performing certain tasks. By locking the bendable sections at a particular position, this enables the surgeon to be more hands-free for controlling other degrees of freedom of the instrument such as manipulation of the rotation knob 24 and, in turn, orientation of the end effector.

The instruments shown in respective FIGS. 1 and 2 are primarily of the same construction with the exception that the control lever for tool actuation is somewhat different in the two embodiments. In both of these embodiments the handle is of a pistol grip type. In FIG. 1 the lever 22 has multiple indentations for one or more fingers and a release button on the handle disposed in facing relationship to the lever. In the embodiment of FIG. 2 the lever 22' has a single finger hole for controlling the lever and also includes a similar release button. The release button is used to release the actuated or closed tool and is identified in both of the disclosed embodiments as button 96.

In the first embodiment, the instrument is illustrated with the handle end of the instrument tipped downwardly in the direction of arrow V. This movement bends the instrument at the proximal bendable member 18, as can be seen in FIG. 1. This action, in turn, bends the distal bendable member upwardly as also shown in FIG. 1. As mentioned before, opposite direction bending can be used by rotating or twisting the control cables through 180 degrees.

One feature of the present invention is the ability for both locking and rotating the instrument, controlled from a single control element, preferably controlled at the rotation knob 24. In a preferred embodiment of the present invention the angle locking means 140 is engaged by axially displacing the rotation knob, such as by pulling on the rotation knob 24 in a proximal direction into the handle. The locking feature can be released or disengaged by pushing on the knob 24 in a distal direction as described in further detail hereinafter.

In both embodiments described herein, the handle 12 is in the form of a pistol grip and includes a horn 13 to facilitate a comfortable interface between the action of the surgeon's hand and the instrument. FIG. 1 shows the hand position relative to the instrument handle. A jaw clamping lever 22 is shown in FIG. 1 pivotally attached at the base of the handle. The lever 22 actuates a slider (not shown in FIG. 1 but shown in FIG. 2) that controls a tool actuation cable that extends from the slider to the distal end of the instrument. FIG. 1 also shows a jaw release button 96 that is located on the inside of the handle 12 just above the pivot for the jaw clamping lever 22. As will be described in more detail hereinafter, the button 96 engages the slider in a ratcheting action until released by pushing on it as indicated by the arrow M shown in FIG. 3.

The shape of the handle allows for a comfortable substantially one-handed operation of the instrument as shown in either FIG. 1 or FIG. 2. As shown in FIG. 1, the surgeon may grip the handle 12 between his palm and middle finger with the horn 13 nestled in the crook between his thumb and forefinger. This frees up the forefinger and thumb to rotate the rotation knob 24 using the finger indentions 31 that are disposed on the peripheral surface of the rotation knob. This arrangement also makes it possible to be able to push and pull on the rotation knob 24 to engage or disengage the angle locking means. FIG. 13 shows the rotation knob in its released position with it in its more distal position separated from the handle. FIG. 14 shows the rotation knob in its locked position having been moved proximally toward the handle. In both locked and unlocked positions the rotation knob is capable of controlled rotation to control axial rotation at the tip of the instrument about axis P.

The jaw clamping lever 22 may be engaged by the ring and/or pinky fingers of the surgeon and has at least two indents to accommodate these fingers as shown in FIG. 1. When the surgeon wishes to release the clamped jaws, those two fingers are removed from the lever 22 and one or both of them can then be used to depress the jaw release button 96. A return spring 82 in the handle (FIG. 2) opens the jaws and returns the lever 22 to its relaxed position upon activating the release button 96.

A second preferred embodiment of the instrument is shown in FIG. 2. Further details of this instrument are shown in FIGS. 3-16. In this embodiment an alternate jaw clamping lever 22' is shown. In this version there is provided a fingertip engaging recess in a gimbaled ball 27 instead of two finger indentions. The free end of the lever 22' supports the gimbaled ball 27 which has a through hole or recess 23 which receives one of the fingers of the user. The ball 27 is free to at least partially rotate in the lever end. The surgeon may grip the handle between the palm, ring and pinky fingers with the horn 13 nestled in the crook between his thumb and forefinger and operate the rotation knob 24 as previously described. The surgeon may then operate the jaw clamping lever 22' with the forefinger or middle finger as shown in phantom outline in FIG. 2.

Figure 2A:
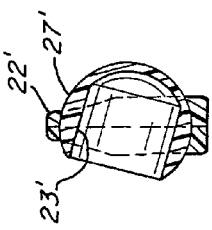
FIG. 2A is a cross-sectional view of an alternate embodiment of the finger gimbal.

FIG. 2A illustrates an alternate preferred embodiment of the finger gimbal arrangement in a cross-sectional view. This is also in the form of a ball in a socket, in which the ball is free to be rotated in the socket, and in which the socket is defined in the lever free end. In this embodiment, rather than having the hole go completely through the ball there is provided a blind hole 23' in the ball 27'. The ball is free to rotate in the lever end and thus the ball can also be rotated to alternate positions corresponding to either a left-handed or right-handed user. The blind hole enables the user to have a firmer grip of the lever and thus enhanced control of the lever action.

In the first embodiment the lever 22 can be controlled primarily by pressing inwardly on the lever. However, in the second embodiment as illustrated in FIG. 2, the surgeon can have greater control of the lever 22', as this arrangement allows the surgeon to push or pull the lever precisely rather than just a pull and release action. In the embodiment in FIG. 2 the surgeon can use the pinky or ring finger to squeeze the jaw release button 96 to disengage the ratchet mechanism and thus release the tool. In another version of the invention the return spring 82 may be eliminated in order that the jaws may be operated entirely under the control of, for example, the index or forefinger disposed in the recess 23. This version of the invention is most advantageous when using an end effector such as scissors, whereas the embodiment shown in FIG. 1 would be best utilized with an end effector such as a needle driver or clamp.

Reference is now made to FIGS. 2-16 for further details of the second embodiment of the invention. In this embodiment the distal bending member 20 is shown without the sheath 98 so as to provide the details of the distal bendable member 20. The distal bendable member is shown as comprised of spaced discs 110 that define therebetween the spaced slots 112. Ribs 111 connect between adjacent discs 110 in a manner similar to that described in the aforementioned U.S. application Ser. No. 11/185,911.

As indicated previously, the end effector or tool 16 is actuated by means of the jaw actuation means 30 which is comprised primarily of the elongated lever 22'. The lever 22' is supported from the housing at the lever pivot pin 72. Refer to FIGS. 2 and 3. The closing of the lever 22' against the handle 12 acts upon the slider 28 which is used to capture the very proximal end of the actuation cable 38. When the slider 28 is in the position depicted in FIG. 2, it is noted that the end effector jaws are fully open. See also FIG. 4A. In that position the slider 28 is disposed at the more distal end of the slideway 84. The slideway 84 is part of the internal support in the handle 12. When the slider 28 is moved proximally, as depicted in FIG. 3, then the jaws 44 and 46 are moved toward a closed position. In FIG. 3 the jaws are illustrated as closing so as to grasp a needle 45. See also FIG. 4B. In that position the slider 28 has moved to the more proximal end of the slideway 84. FIG. 3 shows the distal end of the slider spaced the dimension D1 from an end wall of the slideway 84. FIG. 2, on the other hand, shows the slider contacting that same end wall.

The instrument shaft 14 includes an outer shaft tube 32 that may be constructed of a light weight metal material or may be a plastic material. The proximal end of the tube 32 is received by the adaptor cover 26. The distal end of the tube 32 is secured to the distal bendable member 20. Within the outer shaft tube 32 there is provided a support tube 34 that is preferably constructed of a plastic material. Tube 34 extends between the distal bendable or flexible member 20 and the proximal bendable or flexible member 18. The jaw actuator cable 38 extends within this support tube 34. The support tube 34, as depicted in FIG. 3, supports along its length a plurality of spacers 36. There are preferably multiple spacers disposed along the support tube 34. Each of the spacers 36 is preferably evenly spaced and each may be provided with diametric guide slots (not shown). There may be four such guide slots disposed at 90 degree intervals about each spacer 36 for accommodating the respective cables.

Refer also now to FIGS. 4A-4D for further details of the tool end of the instrument. The end effector 16 is comprised of a pair of jaws 44 and 46. As indicated previously these jaws may be used to grasp a needle 45 or other item. The upper jaw 44 fits within a channel 47 in the lower jaw 46. A pivot pin 48 is used between the jaws to enable rotation therebetween. A translation pin 42 extends through the slot 50 of jaw 46 and the slot 52 of jaw 44 and engages with the hole in the distal cable end connector 40. The connector 40 is secured to the very distal end of the jaw actuator cable 38 and is positioned within a channel of the jaw 44. When the lever 22' is in its rest position, as depicted in FIG. 2, the jaws are fully open. In that position the pin 42 is at a more distal location maintaining the jaws in an open position. As the cable 38 is pulled, such as proximally in FIG. 3, then the pin 42 moves to the right in the slots 50 and 52 causing the jaws 44 and 46 to pivot toward a closed position.

FIGS. 4A-4D also depicts an end wall or plate 54 of the jaw 46. One end of the distal bendable member 20 is urged against this end wall 54. The member 20 may be secured to the wall 54 by an appropriate means. In one embodiment, the cabling tension itself of the instrument holds the members together. On the end wall 54 there are disposed a pair of anchors 56 and 58 for the flex control cables 100. FIG. 4D illustrates four such cables 100. The distal end of the distal bendable member 20 may be provided with pockets for receiving the anchors 56 and 58. The anchors 56 and 58 are firmly attached to the end wall 54.

The jaw actuator cable 38 terminates at its respective ends at the end effector and the rotation barrel 66 (see FIG. 3).

Within each of the bendable sections or bendable members 18 and 20 there is provided a plastic tube. This includes a distal tube 60 and a proximal tube 62. Both of these tubes may be constructed of a plastic such as polyethyletherkeytone (PEEK). The material of the tubes 60 and 62 is sufficiently rigid to retain the cable 38 and yet is flexible enough so that it can readily bend with the bending of the bendable members 18 and 20. The tubes have a sufficient strength to receive and guide the cable, yet are flexible enough so that they will not kink or distort, and thus keep the cable in a proper state for activation, and also defines a fixed length for the cable. The tubes 60 and 62 are longitudinally stiff, but laterally flexible.

FIG. 4A depicts the jaws in a fully open position. FIG. 4B depicts the jaws grasping a needle. FIG. 4C depicts the jaws fully closed. FIG. 4D is a cross-sectional view taken along line 4D-4D of FIG. 4C.

The proximal bendable member 18 may also be constructed as a unitary or uni-body slotted structure including a series of flexible discs 130 that define therebetween slots 132. A "unitary" or "uni-body" structure may be defined as one that is constructed for use in a single piece and does not require assembly of parts. Connecting ribs 131 may extend between adjacent discs. Clearance holes are provided in the discs and/or ribs for accommodating the four bend control cables 100. The proximal bending member 18 also has four additional passages for the locking cables 160 and a conical distal end portion 19. The conical portion 19 is provided with four recesses 163 (FIGS. 13 and 15) for cable anchors 162 for cables 160. The conical portion 19 also has four guide grooves 107 that match up with four guide grooves 106 in the adapter 26 (FIG. 15) to channel the bending cables 100 to the outer shaft 32. The rotation knob 24 houses an insert collar 104 which in turn seats the proximal end of the proximal bending member. Both of the bendable members preferably have a rib pattern in which the ribs (111, 131) are disposed at a preferred 60 degree variance from one rib to an adjacent rib. This has been found to provide an improved bending action. It was found that by having the ribs disposed at intervals of less than 90 degrees therebetween improved bending was possible. The ribs may be disposed at intervals of from about 35 degrees to about 75 degrees from one rib to an adjacent one. By using an interval of less than 90 degrees the ribs are more evenly distributed. Refer to FIG. 7 for an illustration of ribs at 60 degrees to each other. As a result the bending motion is more uniform at any orientation. In the present invention both of the bendable members may be made of a highly elastic polymer such as PEBAX (Polyether Block Amide), but could also be made from other elastic and resilient materials.

The handle 22' in FIG. 2 is shown in the lowermost position which is considered as the "at rest" position. This would be achieved by either action of the return spring 82 in the bore 80 of the slide 28 in certain instruments or by the surgeon manually moving the lever to that position in other embodiments of the instrument where a return spring is not desired.

FIG. 3 illustrates the lever 22' passing through a slot 73 in the handle and being mounted to a pivot pin 72. An arm 70 of the lever 22' has a cylindrical head 71 which mates with a recess 74 in a boss 75 at the proximal end of the slider 28. The slider 28 sits in the slideway 84 and moves proximally and distally in response to the lever position and/or return spring action. The slider 28 carries a rotatable barrel 66 clamped to the push/pull cable 38 by means of a set screws 67. The barrel 66 is rotatable in response to the rotation of the instrument shaft and end effector. Refer also to FIG. 5 for further details of the slider mechanism. The barrel 66 sits in a slot 68 which is open to contiguous slot 78 at one end and is closed by a wall 69 at its other end. The wall 69 has a through hole which acts as a guide for the push/pull cable 38 that protrudes from the proximal end of the barrel 66, and thus guides the barrel action itself. The barrel 66 is urged against the wall 69 by a compression spring 76 that is disposed in the slot 78. The position of the lever, as depicted in FIGS. 2 and 5 has the jaws fully open as also shown in FIG. 4A.

As the lever is squeezed toward the handle, the slider 28 is urged proximally against the pressure of the return spring 82 which is a compression spring; that is if one is used. The lever 22' is shown in three different positions in FIG. 3. The position of FIG. 2 is shown in FIG. 3 by the lowermost phantom lines. The middle position, also shown in phantom lines, is approximately the position where the slider 28 has traveled a distance D1 (in FIG. 3) and that the moveable jaw 44 has contacted an item such as the needle 45. This is the position of the slider 28 shown in FIG. 5 and with the jaws shown in the position in FIG. 4B grasping the item. From that position, further movement of the slider 28 proximally results in the barrel 66 sliding distally relative to the slider, thus lifting off the end wall 69 defined by the slot 68. See the dimension D2 in FIG. 3. This action causes the spring 76 to apply jaw clamping pressure on the needle, by further tensioning the cable 38. When that position is reached, the barrel 66 and cable 38 substantially cease linear movement but the lever 22' can be fully squeezed until the position shown in full line in FIG. 3 is reached. At that position, as depicted in FIG. 3, the stop 29 on the lever 22' contacts the handle 12 and the slider 28 stops just short of the end wall of the slideway 84, imposing a maximum pressure on the needle.

A ratcheting action between the release button 96 and the slideway 84 prevents the slider 28 from any return motion until the release lever or button 96 is pushed. The release button 96 is mounted on a pivot pin 90 and has a pawl 94 that engages the teeth 86 on underside of the slider 28. The pawl 94 is urged into contact with the teeth on the slider 28 by means of an integral leaf spring 92. The thickness t (FIG. 4B) of an item grasped by the jaws is adjusted for by the sliding action of barrel 66. The distance D2 shown in FIG. 3 is determined by the thickness t or in other words is a direct function of the thickness t. This dimension also accommodates any proximal movement of the cable 38 when the knob 24 is pulled back to lock in the angle of the bendable members.

FIG. 3 shows the surgical tool grasping an item such as a needle and shows the end effector being bent at an angle B2 in response to the handle being bent at angle B1 to the instrument shaft. The resulting tilt of the universal ring 142 of the angle locking means 140 is also shown but the cables 160 that control the tilt are not shown for simplicity as they lie in a plane behind the cables 100 illustrated in FIG. 3. The cables 160 and their connections are shown in detail in FIGS. 13-16.

The proximal bending member 18 has discs 130, slots 132 and connecting ribs 131 similar to the previous instrument but has four additional passages for respective cables 160 and a conical distal end portion 19 with four recesses 163 for cable anchors for cables 160. The conical portion has four elongated guide grooves 107 that match up with four like guide grooves 106 in the adapter 26. These matching grooves form a channel for capturing the bending cables 100 as they extend from the proximal bendable member into the outer shaft 32.

The rotation knob 24 houses an insert collar 104 which in turn seats the proximal end of the proximal bending member 18. The rotation knob 24 and collar 104 have mating features for engagement therebetween so that they rotate together. The rotation knob 24 has diametrically disposed internally facing ridges 25 which engage matching mating channels 105 in insert collar 104, as most clearly shown in FIG. 15. During assembly, the cables 100 which protrude from the proximal end of the proximal bending member 18, after the assembly of the end effector 16, inner and outer shafts 32, 34, adapter 26 and proximal bending member 18, are passed through the four terminal wire crimps or lugs 102 which are keyed into passages in the insert collar 104. The cables are tensioned and crimped and excess cable material is trimmed off. This arrangement holds all the elements together between the end effector 16 and insert collar 104 and, in turn, the rotation knob 24.

The locking cables 160 are anchored distally at 162 at the distal end of the proximal bending member and pass through passages in the proximal bending member and the insert collar 104, as shown in the cross-sectional view of FIG. 13. The cables then pass through passages in the rotation knob 24 and terminate at 164 at the universal ring 142. The insert collar 104 and rotation knob 24 are mated together by means of the ridges 25 and channels 105. The locking cables 160 are tensioned and anchored proximally at terminating end 164 and excess cable material is trimmed off.

The rotation knob 24 has a central aperture into which a cone plunger 180 passes. The cone plunger 180 has a hub 184 at its distal end which is captured between the rotation knob 24 and insert collar 104. The retaining ring 186 holds the plunger 180 relative to the rotation knob 24. Refer to FIGS. 5, 8 and 13. Mounted over the cone plunger 180 is an expansion sphere 144 which in turn carries the rider 148 and universal ring 142. The universal ring 142 is held on the rider 148 by a retaining ring 150 as best seen in FIGS. 13-16. It is the relative axial movement between the cone plunger 180 and the expansion sphere 144 that provides the basic locking action and it is the axial transition of the rotation knob 24 that initiates this action.

The expansion sphere 144 has preferably eight partially spherical petals 146 at the end of a main shank 152. Refer also to the cross-sectional view of FIG. 9 for an illustration of the petals 146. The eight petals 146 form an expandable sphere with a conical cavity in the center shaped to accommodate the cone plunger 180. The expansion sphere 144 is adapted for limited axial sliding within the handle housing upon engagement with the cone plunger 180, but with no rotation between the expansion sphere 144 and the handle. The expansion sphere 144 is adapted to move only a slight distance axially, and in another embodiment may be supported so that it is axially fixed in position. The expansion sphere 144 is provided with interlock means with the handle 12. The shank 152 of the expansion sphere 144 has two mating means in the form of keys 156 that align with mating keyways 157 on the sides of a passage 168 through wall 166 of handle 12. This interlocking allows the expansion sphere 144 to slide in and out of the handle 12 axially, but without rotating.

At the proximal end 154 of the shank 152 there are two opposed flexible fingers 158 that interact with retention means 194 on the handle to effect the locking and releasing of the conical ramped surface 182 within the conical cavity of the sphere. Basically, pulling on the knob 24 toward the handle pushes the cone plunger 180 into the expansion sphere 144. This action in turn causes the proximal end 154 of the shank 152 to contact the wall 196. Retaining ring 150 may act as a thrust washer in this respect. The spring arms 190 of the fingers 158 are urged outwardly by the cone shaped ramped surface 188, as seen in FIG. 14. This causes a ratcheting action at 194. There is an elastic band 192 to help retract the fingers 158 when the knob 24 is pushed forward (distally) once the fingers 158 move off of the ramp surface 188.

FIGS. 13 & 14 illustrate the locking action. FIG. 13 shows the "at rest" position of the angle locking means 140 and FIG. 14 shows how the cables 160 push and pull the universal disc in response to the bending of the proximal bending member and also shows the knob 24 pulled back, as illustrated by the arrow S. The resulting expansion by the plunger is illustrated by the arrows E that exerts a force that bears upon the inside of the rider 148 and hold it tightly in place while allowing the universal disc 142 to rotate freely around the raceway formed by the rider 148 and the retaining ring 150.

The locking mechanism that is described herein is in the form of a follower mechanism 140 that is disposed proximally of the rotation knob. The proximal motion member comprises a proximal bendable member and a plurality of locking cables 160 that intercouple between the follower mechanism and the proximal bendable member. In the present invention the locking occurs by means of the use of a separate follower member illustrated as locking mechanism 140. This follower mechanism operates in conjunction with lock cables 160 to lock a particular position of the proximal bendable member, and by doing so also locking the position of the distal bendable member, as the proximal and distal bendable members are interconnected by actuation cables 100.

Figure 15:
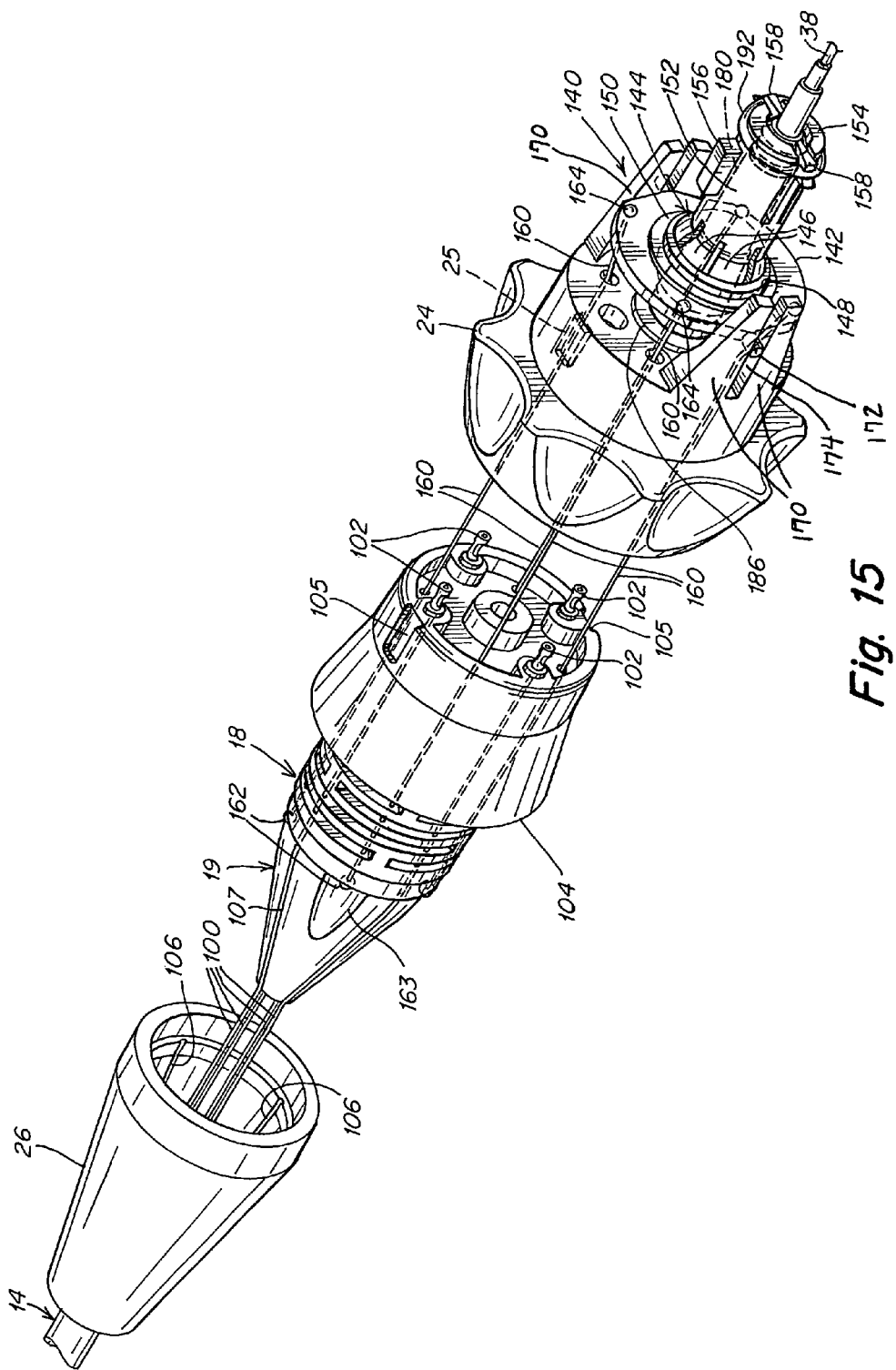
FIG. 15 is an exploded perspective view at the proximal bendable member and rotation knob, and illustrating further details of the angle locking member of FIG. 13.
Figure 16:
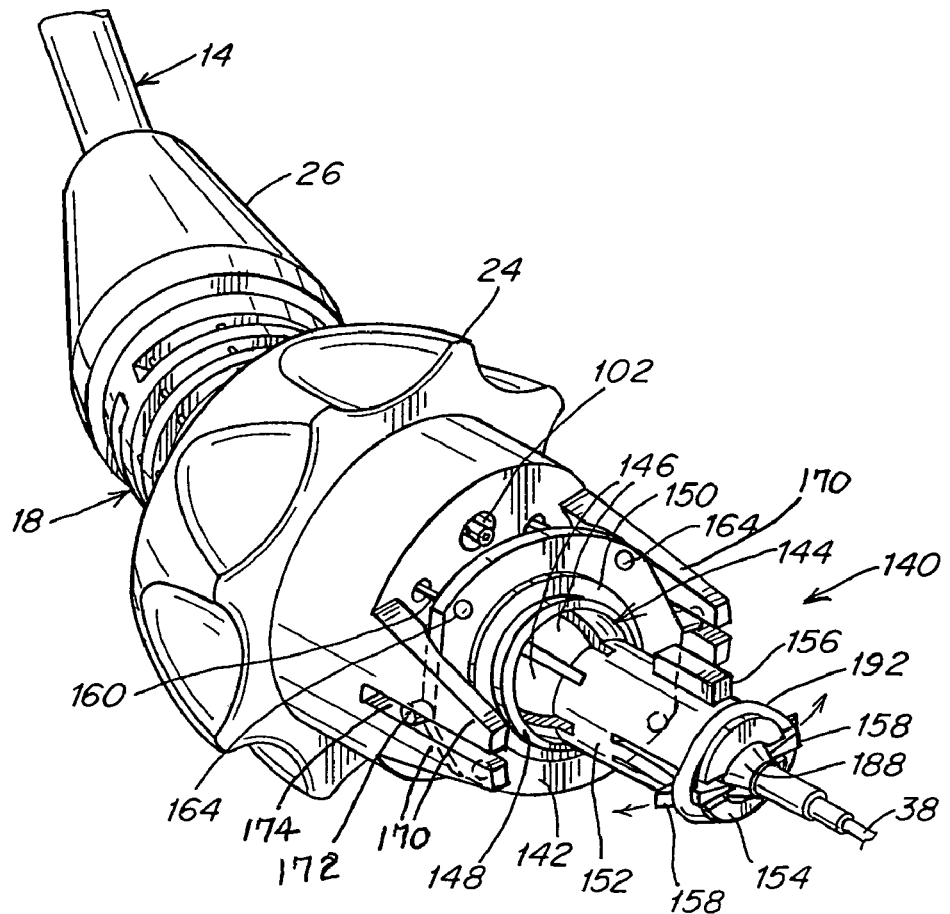
FIG. 16 is a fragmentary perspective view of the assembled proximal bendable member, rotation knob and locking mechanism of FIG. 15, but showing the proximal bendable member locked in a bent position relative to the instrument handle.

The locking mechanism 140 includes, inter alia, the anchor ring 142 that provides the primary support for the locking cables 160, as well as the support of the locking mechanism from the rotation knob structure. In this regard, the anchor ring 142 includes diametrically disposed pins 172 that are accommodated in elongated slots 174 of the opposed rearwardly extending fingers or arms 170. Refer in particular to FIGS. 15 and 16. The fingers 170 extend from the rotation knob barrel. This pin and slot arrangement enables the locking mechanism 140 to move with the bending and rotation action.

When the instrument illustrated in this embodiment is in a straight in-line position then the locking mechanism, and particularly the anchor ring 142 extends substantially transverse to the center axis, as shown in FIG. 13. When the handle 12 is bent, such as in the positions shown in FIG. 14 then it is noted that the follower locking mechanism 140 tilts relative to the longitudinal axis T. When it is desired to lock the mechanism in a particular bent condition then the rotation knob is moved proximally (position of FIG. 14), the cone plunger 180 engages the expansion sphere 144 and this locks the position of the anchor ring 142 and thus also locks the position of the locking or anchor cables 160. This, in turn, locks the position of the proximal bendable member 18 and via the cables 100 also locks the position of the distal bendable member 20. The rigidity of the locking cables 160 maintains the proximal bendable member 18 in the locked position. The cables 160 are preferably substantially larger in diameter than the actuation cables 100 and are thus more rigid than the actuation cables.

Each of the cables 160 are disposed 90 degrees apart, as are the bent cables 100. Refer to FIG. 7 for an illustration of the placement of these cables. It is noted that the cables 160 are disposed 45 degrees to the cables 100. This 45 degree different position is illustrated in FIGS. 7, 8 and 16. The distal end of each cable 160 terminates at lug end 162. As indicated previously, the proximal end of each cable 160 terminates at lug 164. A spring or resilient member may be associated with each termination 164, but is not preferred. Rotation of the rotation knob 24 causes rotation of the entire proximal bendable member and the locking mechanism 140.

The locking mechanism 140 includes, in addition to the anchor ring 142, the rider 148 and the retaining ring 150. Fastening screws or the like may be used for securing together the rider 148 and the retaining ring 150 about the expansion sphere 144 as illustrated in FIGS. 13 and 14. FIG. 3 is a cross-sectional view of the instrument of this embodiment with the handle bent at an angle B1 which causes a corresponding bending at the distal end of the instrument at an angle B2 to the longitudinal shaft axis. In this embodiment the instrument can also be controlled in any direction including directions in and out of the plane of the paper. It is noted that the handle is bent downwardly causing a corresponding bending upwardly of the distal end of the instrument. As indicated previously the cable lengths of the cables 160 are the same and thus when the handle is bent in the manner illustrated in FIG. 3 the locking mechanism 140 tilts relative to axis T and essentially follows the positioning of the proximal bendable member. The locking mechanism 140 has the ability to tilt at any angle, can be controlled to lock the cables 160 and thus the end effector position, but is able to rotate with rotation of the knob 24.

FIG. 14 illustrates the same instrument illustrated in FIG. 13 but with the handle now tilted upwardly so as to provide a corresponding downward tilting at the distal end of the instrument. It is also to be noted that, with this direction of position of the handle, the follower mechanism 140 tilts in the opposite direction to that illustrated in FIG. 3. In the illustrative position of FIG. 14 with the instrument locked the distal part of the instrument can be rotated via the rotation knob 24. This is because, even though the rider 148 is essentially locked with the expansion sphere 144, the universal ring 142 is free to rotate upon rotation of the rotation knob 24. In this locked position the universal ring 142 rotates in its own plane. The rotation causes the distal end of the instrument to rotate the tip (end effector) about a distal tip axis such as shown by the axis P in FIG. 3. The rotation occurs effectively even though the instrument is locked as to its position. In other words the orientation of the instrument can be changed by rotating the knob 24, even though its position is fixed.

The instrument of the present invention provides an improved instrument, particularly from the standpoint of ease of use by the surgeon. The lever arrangement permits fine control by the user, particularly the embodiment that has the recess gimbal arrangement where the finger of the user can be engaged with the lever. Another feature is the combination of use of the rotation knob so that it functions, not only for rotation of the distal tip of the instrument, but also functions as the means by which the instrument can be locked in a particular position. This includes the preferred axial displacement of the rotation knob to perform the locking function. In an alternate embodiment of the present invention the rotation knob may move distally to lock rather than proximally by rearranging the plunger and expansion sphere. In another version of the present invention another form of rotation mechanism may be used such as a slide mechanism to control distal rotation about the tool tip axis. A locking function is still associated with such an arrangement, such as by depressing the slide mechanism to provide the lock function.

Having now described a limited number of embodiments of the present invention it should now be apparent to one skilled in the art that numerous other embodiments and modifications are contemplated as falling within the scope of the present invention as defined by the appended claims.

What is claimed is:

1. A surgical instrument comprising:
    an instrument shaft having proximal and distal ends;
    a tool disposed from the distal end of the instrument shaft;
    a control handle disposed from the proximal end of the instrument shaft;
    a distal motion member for coupling the distal end of said instrument shaft to said tool;
    a proximal motion member for coupling the proximal end of said instrument shaft to said handle;
    actuation means extending between said distal and proximal motion members for coupling motion of said proximal motion member to said distal motion member for controlling the positioning of said tool;
    a rotation knob disposed adjacent the control handle and rotatable relative to the control handle for causing a corresponding rotation of the instrument shaft and tool;
    and a locking mechanism for fixing the position of the tool at a selected position and having locked and unlocked states;
    said rotation knob having a first position in which the rotation knob is controlled to control the locking mechanism to be in its locked state and a second position in which the locking mechanism is released to its unlocked state so as to allow tool positioning;
    said rotation knob constructed and arranged to support the proximal motion member so that upon rotation of said rotation knob relative to said control handle, the proximal motion member, instrument shaft and tool are rotated therewith.

2. The surgical instrument of claim 1 wherein at least said proximal motion member comprises a proximal bendable member and said rotation knob is adapted to rotate the tool about a distal tool roll axis.

3. The surgical instrument of claim 1 wherein said control handle comprises a pistol grip handle having an engagement horn to assist in holding the handle.

4. The surgical instrument of claim 3 wherein said rotation knob is disposed at the distal end of the handle and said horn is disposed proximally of the rotation knob and on the top of the pistol grip handle.

5. The surgical instrument of claim 3 including an actuation lever supported from said pistol grip handle at a pivot point at the proximal end of the handle.

6. The surgical instrument of claim 5 wherein said actuation lever has a free end with a finger loop for receiving a users finger to control the lever.

7. The surgical instrument of claim 5 further including a release button on the handle in juxtaposition to said lever and for releasing the lever from an actuated to released position.

8. The surgical instrument of claim 1 wherein said rotation knob is moved axially from the first to second positions.

9. The surgical instrument of claim 8 wherein the rotation knob is moved toward said handle to activate the locking mechanism and is moved away from the handle to release the locking mechanism.

10. The surgical instrument of claim 1 including a tool actuation cable that extends from said tool to said handle, a slider for capturing the proximal end of said tool actuation cable and an actuation lever supported at said handle for controlling the translation of said slider.

11. The surgical instrument of claim 10 including a slideway for receiving said slider, a pair of springs disposed in said slider and a rotational barrel disposed between said springs and for holding the proximal end of said tool actuation cable.

12. The surgical instrument of claim 1 wherein said locking mechanism comprises a follower mechanism disposed proximally of said rotation knob, said proximal motion member comprising a proximal bendable member and a plurality of locking cables that intercouple between said follower mechanism and said proximal bendable member.

13. A surgical instrument comprising:
    an instrument shaft having proximal and distal ends;
    a tool disposed from the distal end of the instrument shaft;

a control handle disposed from the proximal end of the instrument shaft;
a distal motion member for coupling the distal end of said instrument shaft to said tool;
a proximal motion member for coupling the proximal end of said instrument shaft to said handle;
actuation means extending between said distal and proximal motion members for coupling motion of said proximal motion member to said distal motion member for controlling the positioning of said tool;
a rotation knob disposed adjacent the control handle and rotatable relative to the control handle for causing a corresponding rotation of the instrument shaft and tool;
and a locking mechanism for fixing the position of the tool at a selected position and having locked and unlocked states;
said rotation knob having a first position in which the locking mechanism is controlled to be in its locked state and a second position in which the locking mechanism is released to its unlocked state so as to allow tool positioning;
wherein said locking mechanism comprises a follower mechanism disposed proximally of said rotation knob, said proximal motion member comprising a proximal bendable member and a plurality of locking cables that intercouple between said follower mechanism and said proximal bendable member; and
wherein said locking mechanism further comprises an expandable partial sphere for supporting said locking cables and a plunger engaging with a center passage of said expandable partial sphere, said plunger supported from said rotation knob.

14. A surgical instrument comprising:
an instrument shaft having proximal and distal ends;
a tool disposed from the distal end of the instrument shaft;
a control handle disposed from the proximal end of the instrument shaft;
a distal motion member for coupling the distal end of said instrument shaft to said tool;
a proximal motion member for coupling the proximal end of said instrument shaft to said handle;
cable actuation means extending between said distal and proximal motion members for coupling motion of said proximal motion member to said distal motion member for controlling the positioning of said tool;
said control handle including a handle housing that forms an internal housing space;
a tool actuation lever for controlling said tool and pivotally supported from said control handle;
a rotation knob constructed and arranged relative to the control handle for manual rotation relative to the control handle for controlling the tool so as to rotate about a distal tool axis to, in turn, control the orientation of the tool;
said rotation knob further disposed between the tool actuation lever and at least part of the proximal motion member;
and a locking mechanism for selectively locking the position of the tool and having separate respective locked and unlocked states;
at least part of said locking mechanism being disposed in the control handle internal housing space:
said locking mechanism including an expandable partial sphere and a plunger that engages with a center passage of said expandable partial sphere;
said plunger being axially moveable relative to said expandable partial sphere to control the expansion of said expandable partial sphere:
said locking mechanism constructed and arranged to control said proximal motion member alternatively;
in the unlocked state, enabling operation of the proximal motion member,
in the locked state, locking the position of the proximal motion member which, in turn, via the cable actuation means locks the position of the distal motion member and tool.

15. The surgical instrument of claim 14 wherein said plunger moves proximally from the unlocked to the locked state.

16. The surgical instrument of claim 14 wherein said control handle has proximal and distal sides; said tool actuation lever is supported toward the proximal side of the control handle while the rotation knob is mounted more toward the distal side of the control handle.

17. The surgical instrument of claim 14 wherein said locking mechanism further includes a rider disposed about said expandable partial sphere and at least one locking cable that engages between said proximal motion member and said rider for selectively fixing the position of the motion members, and in turn, said distal tool.

18. The surgical instrument of claim 12 wherein said follower mechanism includes inter-engaging members, one of which is attached to the rotation knob, and the other one of which carries at least one locking cable.

19. The surgical instrument of claim 14 wherein the expandable partial sphere is for supporting at least one locking cable and the plunger is supported from said rotation knob.

20. The surgical instrument of claim 19 including a cable retainer ring supported on the rider and rotatable relative to the rider; said at least one locking cable including a plurality of locking cables that are separate from the cable actuation means and include respective ends thereof supported by the cable retainer ring.

21. The surgical instrument of claim 20 wherein said cable retainer ring is rotatable relative to said rider in both locked and unlocked states.

22. In a medical instrument having a proximal control handle and a distal tool that are intercoupled by an elongated instrument shaft that is meant to pass internally of an anatomic body, proximal and distal movable members that respectively intercouple said proximal control handle and said distal tool with said instrument shaft, cable actuation menas disposed between said movable members for coupling motion of said proximal movable member to said distal motion member for controlling the positioning of said tool, said control handle having proximal and distal ends, an actuation lever at said control handle for controlling said distal tool, a rotation knob disposed adjacent the control ahdnel and rotable relative to the control handle for causing a corresponding rotation of the instrument shaft and tool, and a locking mechanism for fixing the position of the tool at a selected position and having locked and unlocked states, said rotation knob having a first position in which the rotation knob is controlled to control the locking mechanism to be in its locked state and a second position in which the locking mechanism is released to its unlocked state so as to allow tool positioning.

23. The medical instrument of claim 22 wherein said locking mechanism is manually operable by a user and that includes a follower the position of which is responsive to the position of said movable members.

24. The medical instrument of claim 22 wherein said rotation knob is constructed and arranged to support the proximal movable member so that, upon rotation of said rotation knob, the proximal movable member, instrument shaft and tool are rotated therewith.

25. The medical instrument of claim 24 wherein said rotation knob is moved axially from the first to second positions.

26. The medical instrument of claim 22 wherein said control handle includes a pistol grip handle and said actuation lever has a free end with a recess for receiving a finger of the user to control the actuation lever.

27. The medical instrument of claim 26 including a ball supported in a socket at the free end of the actuation lever, said ball having a hole therein that defines said finger recess.

28. The medical instrument of claim 22 wherein said rotation knob has a cavity for receiving at least a portion of the proximal movable member so that, upon rotation of said rotation knob, the movable members, instrument shaft and distal tool all rotate therewith.

29. The medical instrument of claim 28 further including a release button on the control handle in juxtaposition to said actuation lever and for releasing the actuation lever from an actuated to released position.

30. The medical instrument of claim 29 including a slider in said control handle for controlling a tool actuation cable, said actuation lever including a pivot point attached to said control handle and disposed between one end that defines a socket for a rotation gimbal for accommodating the user's finger and another end that engages said slider.

31. The medical instrument of claim 22 wherein said locking mechanism is disposed at said control handle and includes a follower and at least one locking cable that engages between one of said movable members and said follower for selectively fixing the position of the movable members, and in turn, said distal tool.

32. The medical instrument of claim 31 wherein said follower includes inter-engaging members, one of which is attached to the rotation knob, and the other one of which carries the at least one locking cable.

33. The medical instrument of claim 22 wherein the rotation knob is operable to control the distal tool in both locked and unlocked states of the locking mechanism.

34. The medical instrument of claim 22 wherein said locking mechanism is disposed in the control handle and has inter-engaging elements that include a first locking piece responsive to the rotation knob movement and a second locking piece that fixes the position of the movable members.

35. The medical instrument of claim 34 wherein the first locking piece includes a follower and the second locking piece includes at least one locking cable that connects to the proximal movable member.

36. The medical instrument of claim 35 wherein the follower includes an expandable partial sphere for supporting the at least one locking cable and a plunger supported from said rotation knob.

37. The medical instrument of claim 35 including a rider mounted on the expandable partial sphere and a cable retainer ring supported on the rider and rotatable relative to the rider; said at least one locking cable including a plurality of locking cables that are separate from the cable actuation means and include ends thereof supported by the cable retainer ring.

38. A surgical instrument comprising:
an instrument shaft having proximal and distal ends;
a tool disposed from the distal end of the instrument shaft;
a control handle disposed from the proximal end of the instrument shaft;
said control handle including a handle housing that forms an internal housing space;
a distal motion member for coupling the distal end of said instrument shaft to said tool;
a proximal motion member for coupling the proximal end of said instrument shaft to said handle;
actuation cabling extending between said distal and proximal motion members for coupling motion of said proximal motion member to said distal motion member for controlling the positioning of said tool;
a manually operated locking member accessible from the control handle;
and a locking mechanism controlled from said manually operated locking member for fixing the position of the tool at a selected position and having locked and unlocked states;
at least a part of the locking mechanism being disposed in the internal housing space of the control handle;
said locking mechanism including an expandable partial sphere, a plunger that is axially moveable under control of said manually operated locking member to, in turn, control the expansion of said expandable partial sphere, and a rider engagingly disposed about said expandable partial sphere;
whereby the locked state is assumed when the manually operated locking member controls the plunger to move axially to expand the expandable partial sphere to, in turn, lock the position of the rider relative to the expandable partial sphere to fix the position of the proximal motion member and, in turn, the distal motion member and tool.

39. The surgical instrument of claim 38 wherein said expandable partial sphere has a through passage for receiving said plunger.

40. The surgical instrument of claim 39 wherein, in the locked state, the expandable sphere bears against an inner surface of the rider to fix the position of the proximal motion member.

* * * * *